United States Patent
Bonnet et al.

(10) Patent No.: US 11,547,655 B2
(45) Date of Patent: Jan. 10, 2023

(54) **USE OF AN EXTRACT OF THE PERICARP OF *NEPHELIUM LAPPACEUM* FOR HYDRATING THE SKIN AND/OR MUCOUS MEMBRANES**

(71) Applicant: BASF Beauty Care Solutions France S.A.S., Lyons (FR)

(72) Inventors: Isabelle Bonnet, Lyons (FR); Sébastien Cadau, F'Isle d'Abeau (FR); Louis Danous, Saulxures-lès-Nancy (FR); Charlotte Derceville, Nancy (FR); Sabrina Leoty-Okombi, Vaulx Milieu (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 0 days.

(21) Appl. No.: 16/617,011

(22) PCT Filed: Aug. 1, 2018

(86) PCT No.: PCT/FR2018/051973
§ 371 (c)(1),
(2) Date: Nov. 26, 2019

(87) PCT Pub. No.: WO2019/025725
PCT Pub. Date: Feb. 7, 2019

(65) Prior Publication Data
US 2020/0163870 A1 May 28, 2020

(30) Foreign Application Priority Data
Aug. 2, 2017 (FR) ...................................... 1757404

(51) Int. Cl.
*A61K 36/00* (2006.01)
*A61K 8/9789* (2017.01)
*A61Q 19/00* (2006.01)
*A61Q 5/00* (2006.01)

(52) U.S. Cl.
CPC .............. *A61K 8/9789* (2017.08); *A61Q 5/00* (2013.01); *A61Q 19/00* (2013.01); *A61Q 19/007* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 7,049,300 B2 | 5/2006 | Dalko et al. | |
| 2015/0238462 A1 | 8/2015 | Blanchard et al. | |
| 2020/0078291 A1 | 3/2020 | Bardey et al. | |

FOREIGN PATENT DOCUMENTS

| | | | |
|---|---|---|---|
| CN | 105534812 A | | 5/2016 |
| JP | 2001220344 A | | 8/2001 |
| JP | 2002145730 A | | 5/2002 |
| JP | 2008013612 A | * | 1/2008 |
| KR | 20090056521 A | | 6/2009 |
| KR | 101393007 B1 | * | 5/2014 |
| WO | WO-2002051828 A2 | | 7/2002 |
| WO | WO-2011018278 A2 | | 2/2011 |

OTHER PUBLICATIONS

Sun et al. (2010) Journal of Food Biochemistry 35: 1461-1467. (Year: 2010).*
Database WPI Week 200961, Thomson Scientific, London, GB, AN 2009-K31574, XP002779953, 2009, 1 page.
Dr. Marry Josephine R Suganthi A, "*Nephelium lappaceum* (L.): An overview", International Journal of Pharmaceutical Science and Research, vol. 1, Issue 5, Jul. 2016, pp. 36-39.
Search Report for FR Patent Application No. 1757404, dated Apr. 11, 2018, 3 pages.
Sekar, et al., "Formulation and Evaluation of Novel Antiaging Cream Containing Rambutan Fruits Extract", International Journal of Pharmaceutical Sciences and Research, vol. 8, Issue 3, Mar. 1, 2017, pp. 1056-1065.
Thitilertdecha, et al., "Phenolic content and free radical scavenging activities in rambutan during fruit maturation", Scientia Horticulturae, vol. 129, Issue 2, 2011, pp. 247-252.
International Search Report for PCT/FR2018/051973 dated Oct. 18, 2018.
Written Opinion of the International Searching Authority for PCT/FR2018/051973 dated Oct. 18, 2018.

* cited by examiner

*Primary Examiner* — Russell G Fiebig
(74) *Attorney, Agent, or Firm* — Faegre Drinker Biddle & Reath LLP

(57) ABSTRACT

A subject of the present invention is the cosmetic use of a pericarp extract of the plant *Nephelium lappaceum* for maintaining and/or increasing the hydration and/or the barrier effect of the skin and/or of the mucous membranes. The pericarp extract increases involucrin synthesis and the hyaluronic acid content and the synthesis of ATP and of the taurine transporter TAUT. Another subject of the invention relates to a cosmetic care process comprising the topical application of the pericarp extract of *N. lappaceum*. Finally, a subject of the invention relates to the pericarp extract for use, in particular dermatological use, thereof in the treatment and/or prevention of pathological conditions caused by a state of abnormal dryness of the skin and/or of the mucous membranes.

8 Claims, No Drawings

USE OF AN EXTRACT OF THE PERICARP OF *NEPHELIUM LAPPACEUM* FOR HYDRATING THE SKIN AND/OR MUCOUS MEMBRANES

CROSS-REFERENCE TO RELATED APPLICATIONS

This application is a national stage application (under 35 U.S.C. § 371) of PCT/FR2018/051973, filed Aug. 1, 2018, which claims benefit of French Application No. 1757404, filed Aug. 2, 2017, both of which are incorporated herein by reference in their entirety.

The invention relates to the field of cosmetics and pharmacy, more particularly to the field of dermatology.

The skin is a major organ for protection against a certain number of external attacks, in particular stress, pollution, UV radiation, temperature changes. It plays a barrier role, including against dehydration. Certain pathological situations or unfavorable external conditions can cause an imbalance in skin exchanges, inducing, inter alia, a decrease in skin hydration.

Hyaluronic acid is a glycosaminoglycan present in the extracellular matrix (ECM) and the epidermis. It has a structural role and a role as a reservoir of growth factors influencing cell protection, adhesion, migration, differentiation and cell communication. Hyaluronic acid is a known marker for the hydration level of the skin.

Involucrin is a soluble protein synthesized in keratinocytes, allowing the hydration of the horny layer of the skin to be maintained by participating in epidermal differentiation and, consequently, by facilitating the cohesion of the horny layer. The term "barrier effect" is used. Moreover, taurine, a sulfur-containing amino acid derivative which accumulates in the keratinocytes, is an osmolyte. It actively participates in skin hydration by maintaining cell volume and ensuring a positive hydric balance. Its receptor, the TAUT protein, present at the surface of keratinocytes, thus also constitutes another marker for the hydration of the upper layers of the skin.

Cosmetic active agents are already known for their hydrating properties, but there is a constant need in the cosmetics and dermatology field to provide alternative and innovative hydrating active ingredients which make it possible to target several proteins and/or molecules concomitantly.

The applicant has discovered, surprisingly, that a pericarp extract of *N. lappaceum* has the ability to increase the hydration and/or the barrier effect of the skin and/or the mucous membranes, in particular of dry skin and/or dry mucous membranes, more effective than an extract of another part of said plant. The pericarp thus provides an entirely novel and surprising technical effect, as will be demonstrated in the present application.

One of the advantages of the extract according to the invention is that it makes it possible to target several markers concomitantly, in the case in point involucrin, hyaluronic acid and the taurine transporter TAUT. Another advantage is that it is derived from a starting material that is not usually taken advantage of, in other words from a part of the plant, the pericarp, that is not eaten and that is not usually exploited. The country from which the pericarp extract according to the invention originates is Vietnam.

Finally, an additional advantage of the extract according to the invention is that it is easy to produce it on an industrial scale.

The *Nephelium lappaceum* plant, also known as rambutan, is a tree found in south-east Asia, in particular in Malaysia and Indonesia. It is a tree 10 to 20 meters high, producing a large amount of fruit. This fruit, known for its organoleptic properties, contains high amounts of sugars, vitamin C and iron. Decoctions of dried roots or leaves have also been used to combat fever.

The use of rambutan in cosmetic compositions is known. Thus, application CN105534812 discloses a composition having various properties, including skin hydration, said composition comprising a mixture of several extracts of a plant, including rambutan.

Patent application JP2002145730 discloses a seed extract of *N. lappaceum* which has a hydrating activity.

Application WO 2011/18278 discloses the use of a rambutan seed oil for use in a cosmetic composition for hydrating purposes, and more generally for the care of keratin fibers, particularly the hair.

Patent application JP2001220344 discloses the use, in a cosmetic composition, of various extracts of a plant, including rambutan. On the other hand, the use of the pericarp of the plant as hydrating active agent is neither disclosed nor suggested.

Furthermore, patent application US20150238462 discloses the presence of phenolic compounds which may come from plant extracts, for their effect on the prevention of water losses in the skin, increasing the barrier effect, and the treatment of atopical dermatitis. A cosmetic use is described. However, this application does not disclose any extract of *N. lappaceum*. It describes an extract of thyme, an extract of green coffee and an extract of pomegranate. The most active extracts for combating water losses are, without distinction, the extracts of pomegranate and of green coffee, which are preferentially administered orally. Thus, while the extract of pomegranate contains ellagic acid, those skilled in the art cannot deduce from this that the effect of this extract is due to the presence of ellagic acid and they would not therefore be prompted to use this molecule in particular, a fortiori originating from an extract other than that of pomegranate, to combat water losses, nor to increase the barrier effect at the level of the skin.

Finally, Suganthi et al. (2016, International Journal of Pharmaceutical Science and Research, 1, 36-39) describe an extract of *N. lappaceum* for its anti-hypoglycemic, antidiabetic and anti-hypercholesterolemic properties. The presence of geranin is described in the pericarp of the plant. However, this molecule is detected in an ethanolic extract of said plant. Nothing in this document prompts those skilled in the art to use geranin or a pericarp extract of *N. lappaceum* comprising same for any application other than therapeutic. Moreover, nothing prompts the preparation of an extract other than an ethanolic pericarp extract.

Thus, to the knowledge of the applicant, no prior art document discloses the use of a pericarp extract for maintaining and/or increasing the hydration of the skin and/or of the mucous membranes, in particular not dry skin and/or mucous membranes, or for maintaining and/or increasing the barrier effect of the skin or mucous membranes, or else for increasing the radiance of the skin complexion. However, the present invention exhibits the numerous technical advantages mentioned above.

A first subject of the invention is thus the cosmetic use of a pericarp extract of *N. lappaceum* for maintaining and/or increasing the hydration and/or the barrier effect of healthy skin and/or of healthy mucous membranes, advantageously healthy dry skin and/or healthy dry mucous membranes, and/or for increasing the radiance of the skin complexion, in particular by increasing the synthesis of ATP and/or of the taurine transporter TAUT in the skin.

A second subject of the invention relates to a cosmetic care process comprising the topical or oral administration of the extract according to the invention for maintaining and/or increasing the hydration and/or the barrier effect of the skin and/or of the mucous membranes, advantageously dry skin and/or mucous membranes, and/or for increasing the radiance of the skin complexion, in particular by increasing the synthesis of ATP and/or of the taurine transporter TAUT in the skin.

A third subject of the invention relates to the pericarp extract N. lappaceum or a pharmaceutical, preferentially dermatological, composition, for use, advantageously dermatological use, thereof in the prevention and/or treatment of pathological conditions caused by a state of abnormal dryness, such as atopic dermatitis, cracking, eczema and/or ichthyosis.

A first subject thus relates to the cosmetic use of a pericarp extract of N. lappaceum for maintaining and/or increasing the hydration and/or the barrier effect of healthy skin and/or of healthy mucous membranes, advantageously healthy dry skin and/or healthy dry mucous membranes.

The term "cosmetic use" herein is intended to mean a nontherapeutic use, which does not require therapeutic treatment, that is to say which is intended to be applied to all or part of an area of healthy, non-pathological skin or mucous membrane. The expression "area of healthy skin and/or of healthy mucous membrane" is intended to mean an area of the skin and/or mucous membrane to which the extract according to the invention is applied and which is referred to as "non-pathological" by a dermatologist, that is to say which does not have an infection, scar, skin disease or disorder such as candidiasis, impetigo, psoriasis, eczema, acne or dermatitis, or wounds or injuries and/or other dermatoses.

In one embodiment of the invention, the pericarp extract according to the invention is applied to healthy dry skin and/or healthy dry mucous membranes.

The N. lappaceum extract according to the invention is a topically acceptable ingredient. The term "topically acceptable" is intended to mean an ingredient suitable for topical application, which is non-toxic, non-irritating to the skin and/or mucous membranes, which does not induce an allergic response, and which is not chemically unstable. The extract may be used orally or topically. Advantageously, it is used topically. The term "topically" is intended to mean the direct local application and/or spraying of the ingredient onto the surface of the skin and/or mucous membranes.

The term "mucous membrane" is intended to mean the ocular mucous membrane, the vaginal mucous membrane, the urogenital mucous membrane, the anal mucous membrane, the nasal mucous membrane, the oral, labial and/or gingival mucous membrane; preferentially, the labial and/or oral mucous membranes.

The extract can be applied topically to all or part of the body and/or of the face and/or the mucous membranes, advantageously chosen from the legs, feet, underarms, hands, thighs, stomach, chest, neck, arms, torso, back, labial mucous membrane, face and/or scalp, more advantageously the chest and/or face, even more advantageously the face.

For the purposes of the invention, the term "increasing the hydration" is intended to mean an at least 2%, advantageously at least 5%, more advantageously at least 10%, very advantageously at least 15% increase in the hydration of human skin and/or mucous membranes treated in the presence of the extract according to the invention, compared with the hydration of said skin and/or said mucous membranes measured without application of the extract.

In one advantageous embodiment of the invention, the measurement is an in vivo measurement of the hydration parameter by corneometry, advantageously on human skin, more preferentially dry human skin. Advantageously, said measurement is carried out after 2 weeks, 4 weeks and/or 8 weeks, preferentially after 8 weeks. In an alternative embodiment of the invention, it involves an in vivo measurement of the hydration parameter by means of a capacitance, advantageously by means of the instrument known as the MoistureMap MM100® which measures the penetration of an electromagnetic field at the surface of the skin. Preferentially, this measurement is carried out after 2 weeks and/or 4 weeks, more preferentially after 4 weeks. In one particularly advantageous embodiment of the invention, this in vivo measurement of the hydration is carried out on a population of 27 women, advantageously at the level of the cheek, under the conditions described in example 2d).

Moreover, the term "increasing the synthesis of involucrin" is intended to mean an increase in the gene expression of the IVL gene and/or in involucrin protein expression. Advantageously, this is an increase in involucrin protein. In one embodiment, the extract according to the invention increases involucrin protein expression by at least 7%, advantageously by at least 15%, more advantageously by at least 30% and very advantageously by at least 45% in the presence of the extract according to the invention, in comparison with the protein expression detected in the absence of the extract. In one advantageous embodiment, this increase in protein expression is measured in keratinocytes, preferentially normal, that is to say non-pathological, human keratinocytes, more advantageously by an immunohistochemical technique (ELISA assay) in the presence of the pericarp extract of N. lappaceum, very advantageously prepared under the conditions described in example 1a), under the conditions described in example 2a).

The term "increasing the hyaluronic acid content" is intended to mean an increase in the hyaluronic acid content of at least 10%, advantageously of at least 15%, more advantageously of at least 40%, very advantageously of at least 50%, in the presence of the extract according to the invention, in comparison with the content detected in the absence of the extract. In one embodiment, this increase is measured in keratinocytes, preferentially normal, therefore non-pathological, human keratinocytes. More preferentially, this increase is an increase in the hyaluronic acid content measured by an immunohistochemical technique (ELISA assay) in the presence of the pericarp extract prepared according to example 1a) under the conditions described in example 2b).

The use of the pericarp extract according to the invention is thus for increasing involucrin synthesis and/or the hyaluronic acid content in the skin and/or the mucous membranes.

The term "increasing the barrier effect" of the skin and/or of the mucous membranes is intended to mean increasing the thickness of the epidermis and/or promoting the cohesion of the horny layer in the skin and the mucous membranes. The term "maintaining the barrier effect" is in addition intended to mean limiting the water losses in the skin and/or the mucous membranes. The use of the extract according to the invention is thus for maintaining and/or increasing the barrier effect in the skin and/or the mucous membranes, in particular by increasing involucrin synthesis.

On the other hand, the pericarp extract according to the invention is preferentially not used to protect the skin and/or the mucous membranes against oxidation, or against skin aging. In one particularly preferred embodiment of the invention, it is not a question of an anti-aging active agent or of an antioxidant or free-radical scavenging active agent.

The term "increasing the synthesis of ATP" is intended to mean an at least 10%, advantageously at least 20%, more advantageously at least 60%, very advantageously at least 90% and further very advantageously at least 120%, increase in the presence of the extract according to the invention, in comparison with the ATP level measured in the absence of the extract. In one advantageous embodiment of the invention, this is an increase measured in fibroblasts, preferentially normal, that is to say non-pathological, human fibroblasts, in the presence of the pericarp extract prepared according to example 1a). More advantageously, the increase in ATP synthesis is measured by bioluminescence (ATP Bioluminescence kit, Roche Diagnostics France) in the presence of luciferase, under the conditions described in example 3a).

Finally, the term "increasing the synthesis of the taurine transporter TAUT" is intended to mean an increase in TAUT synthesis of at least 10%, advantageously 20%, more advantageously of at least 40%, very advantageously of at least 60%, and further very advantageously of at least 80% in the presence of the extract according to the invention, in comparison with the TAUT content measured without extract. In one advantageous embodiment, the increase in the synthesis is measured in keratinocytes, advantageously normal, therefore non-pathological, human keratinocytes. More advantageously, the measurement of the TAUT synthesis is carried out in the presence of the pericarp extract prepared according to example 1a), very advantageously by protein assay, preferentially using the Bradford method. More advantageously, this synthesis is related to the total protein content, under the conditions described in example 3b).

Moreover, the term "maintaining the hydration" of the skin and/or of the mucous membranes is intended to mean preventing the skin and/or the mucous membranes from dehydrating. In one advantageous embodiment of the invention, the extract of *N. lappaceum* increases the hydration of healthy dry skin and/or healthy dry mucous membranes. The term "dry skin" is intended to mean herein dehydrated healthy skin, with no pathological condition and not requiring therapeutic treatment, but which is accompanied by unesthetic and/or uncomfortable manifestations such as itching, tightness, dehydration lines, a rough appearance and/or feel, or a loss of radiance of the complexion, that is to say a dull skin.

The cosmetic use of the pericarp extract of *N. lappaceum* is thus also for increasing the radiance of the skin complexion, in particular by increasing the synthesis of ATP and/or of the taurine transporter TAUT. The extract according to the invention is thus of use and used for stimulating cell metabolism, in particular as an energizing cosmetic active ingredient.

The term "increasing the radiance of the complexion" of the skin is intended to mean a decrease in the dull complexion and/or in the yellowing of the skin of at least 2%, preferentially of at least 4%, more preferentially of at least 6%, after application of a cream comprising the extract according to the invention, in comparison with a placebo cream not comprising the extract. Advantageously, this increase in the radiance of the complexion is measured after 15 days, 28 days and/or 56 days, more advantageously at the level of the face of a population of women. In one advantageous embodiment of the invention, the increase in the radiance of the complexion is evaluated by measuring the luminescence of the skin, advantageously by measuring the parameter L*. Said parameter can be measured by several techniques chosen from chromametry or image analysis. Advantageously, the parameter L* will be measured by chromametry.

In one alternative embodiment of the invention, the radiance of the complexion is measured by clinical assessment. It may be carried out using an instrument of Goniolux® type or by image analysis. Advantageously, it will be carried out by image analysis.

The pericarp extract according to the invention is obtained from a part of the plant comprising the pericarp. Advantageously, the pericarp extract contains only pericarp.

For the purposes of the present invention, the term "pericarp" is intended to mean the shell of the fruit from which the seeds and the pulp have been removed. The pericarp is not therefore the fruit.

In one preferential embodiment of the invention, the pericarp extract according to the invention is not used in combination with a fruit extract of *Litchi chinensis*. In one alternative embodiment of the invention, the pericarp extract is not used with a fruit extract of *L. chinensis* in a cosmetic and/or dermatological, advantageously cosmetic, composition.

In one preferred embodiment of the invention, the pericarp extract contains non-effective concentrations of ellagitannins, advantageously of ellagic acid ($C_{14}H_6O_8$; CAS No. 476.66.4; molecular weight 302.194 g/mol). More preferentially, the pericarp extract according to the invention also contains non-effective concentrations of gallic acid ($C_7HEOs$; CAS No. 149-91-7; molecular weight 170.12 g/mol) and/or chlorogenic acid ($C_{16}H_{18}O_9$; CAS No. 327-97-9; molecular weight 354.311 g/mol) and/or caffeic acid ($C_9H_8O_4$; CAS No. 331-39-5; molecular weight 180.159 g/mol) and/or p-coumaric acid ($C_9H_8O_3$; CAS No. 50940-26-6; molecular weight 164.16 g/mol) and/or ferulic acid ($C_{10}H_{10}O_4$; CAS No. 537-98-4; molecular weight 194.186 g/mol) and/or geranin ($C_{41}H_{28}O_{27}$; CAS No. 60976-49-2; molecular weight 952.648 g/mol).

In one particular embodiment of the invention, the pericarp extract according to the invention contains non-effective concentrations of both ellagic acid and geranin. Particularly advantageously, the pericarp extract prepared according to example 1a) contains non-effective concentrations of ellagic acid.

In one alternative embodiment of the invention, the cosmetic or dermatological composition according to the invention will contain non-effective concentrations of ellagitannins and/or gallic acid and/or chlorogenic acid and/or caffeic acid and/or coumaric acid and/or ferulic acid and/or geranin and/or ellagic acid. Preferentially, said composition will contain non-effective concentrations of ellagic acid. In one particular embodiment of the invention, the cosmetic or dermatological composition according to the invention will contain non-effective concentrations of both ellagic acid and geranin.

The term "non-effective concentrations" is intended to mean concentrations such that said molecules are not present in sufficient concentration in the pericarp extract and/or in the cosmetic ingredient comprising it and/or in a cosmetic and/or dermatological composition comprising it, for maintaining and/or increasing the hydration and/or the barrier effect of the skin and/or of the mucous membranes, advantageously of healthy dry skin and/or healthy dry mucous membranes.

Advantageously according to the invention, ellagic acid is considered to be present in a non-effective concentration when its concentration is less than or equal to 0.035% (w/w) in the pericarp extract according to the invention, more advantageously in an aqueous extract of pericarp prepared under the conditions described in example 1a). In one alternative embodiment of the invention, ellagic acid is considered to be present in a non-effective concentration when its concentration is less than or equal to 0.007% (w/w) in the cosmetic ingredient, for example a cosmetic ingredient as described in example 4. Alternatively again, ellagic acid is considered to be present in a non-effective concentration when its concentration is less than or equal to $1.4 \times 10^{-4}$% (w/w) in a cosmetic composition, advantageously a cream, more advantageously a cream as described in example 5b).

Likewise, geranin is considered to be present in a non-effective concentration in the pericarp extract when its concentration is less than or equal to 0.25% (w/w) in the extract, advantageously in an aqueous extract of pericarp prepared according to example 1a). Alternatively, geranin will be considered to be present in a non-effective concentration in the cosmetic ingredient when its concentration is less than or equal to 0.05% (w/w) in the cosmetic ingredient, in particular in a cosmetic ingredient as described in example 4. Alternatively again, geranin will be considered to be present in a non-effective concentration when its concentration is less than or equal to $1 \times 10^{-3}$% (w/w) in a cosmetic composition, advantageously a cream, more advantageously a cream as described in example 5b).

Thus, in one advantageous embodiment of the invention, ellagic acid does not increase involucrin synthesis as defined in the present invention, nor does it increase the hydration and/or the barrier effect of the skin and/or of the mucous membranes.

In particular, ellagic acid and/or geranin, preferentially ellagic acid, do not make it possible to stimulate involucrin synthesis, more particularly not in keratinocytes termed normal, that is to say non-pathological, under the conditions described in example 2c).

In yet another advantageous embodiment of the invention, the pericarp extract does not contain chebulic acid ($C_{14}H_{12}O_{11}$; molecular weight 356.239 g/mol; CAS No. 23725-05-5) or chebulinic acid ($C_{41}H_{32}O_{27}$; molecular weight 956.68 g/mol; CAS No. 18942-26-2) or chebulanin ($C_{27}H_{24}O_{19}$; molecular weight 652.470 g/mol; CAS No. 166833-80-3). Very advantageously, the pericarp extract according to the invention is not combined with any plant extract containing it, in particular is not combined with any extract of a plant of the *Terminalia* genus.

The extract can be obtained by various extraction methods known to those skilled in the art, chosen from maceration, hot decoction, by milling including ultrasonic milling, using a mixer, or else the extract can be obtained by extraction in water under subcritical or supercritical conditions (carbon dioxide). Preferentially, the extraction is carried out by maceration.

The extraction may be carried out using dry or fresh matter, advantageously dry matter, in an amount of from 0.1% to 20% by weight, advantageously from 1% to 10%, very advantageously from 5% to 10%, even more advantageously of 10% by weight relative to the total weight of the matter and of the extraction solvent.

The extraction may be carried out at a temperature ranging from 4° C. to 300° C., including ambient temperature, that is to say a temperature of 20° C. In one preferential embodiment of the invention, the extraction will be carried out at a temperature of from 60° C. to 90° C., preferentially from 70° C. to 85° C., more preferentially at a temperature of 80° C.

In one alternative embodiment of the invention, the extraction will be carried out at a temperature of from 4° C. to 25° C., more preferentially from 4° C. to 20° C., more advantageously at ambient temperature, that is to say at 20° C.

In yet another alternative embodiment of the invention, the extraction will be carried out in water under subcritical conditions, at a temperature ranging from 100° C. to 300° C., advantageously from 120° C. to 250° C., more advantageously at 120° C. The extraction can be carried out at a single given temperature or at successive increasing temperatures. In one advantageous embodiment of the invention, the extraction will be carried out at a single temperature of 120° C. In an alternative embodiment, it will be carried out according to a gradient of three increasing temperatures of between 100° C. and 200° C., such as 120° C., 140° C. then 160° C., or 110° C., 130° C. then 150° C., or else 120° C., 145° C. then 170° C.

The term extraction under "subcritical conditions" is intended to mean extraction in the presence of water, under conditions of temperature greater than 100° C. and pressure less than 221 bar, such that the water remains in the liquid state but has a viscosity and a surface tension lower than that of water at ambient temperature, increasing its dielectric constant. Thus, the extraction pressure will between 150 bar and 250 bar, preferentially between 200 and 221 bar, advantageously in a pressure extraction autoclave.

The extraction can be carried out for a period of from 30 minutes to 24 hours, preferentially from 30 minutes to 12 hours, more preferentially for a period of from 1 hour to 5 hours, and more advantageously for a period of from 1 hour to 2 hours. Very advantageously, the extraction will be carried out for a period of 1 hour.

The extract according to the invention may be obtained by extraction in a solvent or solvent mixture, preferably a protic polar solvent, and advantageously in water, an alcohol, a glycol, a polyol, a water/alcohol, water/glycol or water/polyol mixture (such as water mixed with ethanol, glycerol and/or butylene glycol and/or other glycols such as xylitol and/or propanediol, etc.), from 99/1 to 1/99 (w/w), advantageously in water as sole solvent.

In particular, the extract is obtained by aqueous extraction. For the purpose of the present invention, "extract obtained by aqueous extraction" is intended to mean any extract obtained by extraction with an aqueous solution containing more than 60% by weight, advantageously at least 70% by weight, in particular at least 80% by weight, more particularly at least 90% by weight, particularly at least 95% by weight, of water relative to the total weight of the aqueous solution, even more advantageously not containing glycol and in particular not containing alcohol, more particularly only containing water.

In one alternative embodiment, the extract is obtained by extraction in a mixture of propanediol and water in the respective proportion (80, 20; v/v).

In another alternative embodiment of the invention, the extraction may be carried out in the presence of a nonionic surfactant, preferentially chosen from lauryl glucoside sold under the name Plantacare® 1200UP by BASF or else caprylyl/capryl glucoside (Plantacare® 810 UP), preferentially caprylyl/capryl glucoside (Plantacare® 810 UP). The concentration by weight of the nonionic surfactant may be between 0.5% and 5%, advantageously between 0.5 and 1%, more advantageously it will be 1% by weight relative to the total weight of the extract.

Thus, in a first embodiment of the invention, the extract is obtained by maceration, in water as sole solvent, of an amount of 10% by weight of pericarp relative to the total weight of solvent and pericarp, for a period of 1 hour at ambient temperature, that is to say at a temperature of 20° C. The extract obtained is decanted and centrifuged, then the supernatant is filtered, under the conditions described in example 1a).

In a second embodiment, the extract is obtained by maceration, in a water/ethanol mixture (30, 70; v/v) for a period of 1 hour at a temperature of 80° C., of an amount of 10% by weight of pericarp relative to the total weight of solvent and pericarp. The extract is then decanted and centrifuged, then the supernatant is filtered, under the conditions described in example 1b).

In a $3^{rd}$ embodiment, the extract is obtained by extraction, in water as sole solvent, of an amount of 5% by weight of pericarp relative to the total weight of solvent and pericarp, for a period of 1 hour at ambient temperature, that is to say at a temperature of 20° C. The extract obtained is decanted and centrifuged, then the supernatant is filtered, under the conditions described in example 1c).

In a $4^{th}$ embodiment, the extract is obtained by extraction, in water under subcritical conditions, at a temperature of 120° C. under a pressure of 250 bar, of an amount of 10% by weight of pericarp relative to the total weight of the plant and solvent. The crude extract is decanted, centrifuged, then filtered, under the conditions described in example 1d).

Advantageously according to the invention, the extract will be filtered at a cut-off threshold of 0.45 µm.

Additional decolorizing and/or deodorizing steps can be carried out on the extract at any stage of the extraction and according to the techniques known to those skilled in the art. In particular, the extract may be decolorized with activated carbon.

The liquid pericarp extract obtained under the conditions described in examples 1a) to 1d) can then be concentrated by evaporation of the solvent or dried for example by freeze-drying or by spray-drying in the presence of maltodextrins. The extract will then be in powder form.

Thus, in one preferential embodiment of the invention, the extract obtained will be spray-dried in the presence of a concentration by weight of maltodextrins of between 20% and 90%, preferentially between 40% and 80%, more preferentially from 70% to 80% relative to the total weight of the powder obtained. In one particular embodiment of the invention, in particular for use thereof in dermatology, the *N. lappaceum* extract obtained is sterilized.

The extract according to the invention can be used alone in the form of a cosmetic ingredient, or in a cosmetic composition comprising at least one cosmetically acceptable excipient. When it is used alone in the form of a cosmetic or dermatological ingredient, it is preferentially solubilized in an aqueous solution containing glycerin, advantageously present at a concentration of from 60% to 90%, more advantageously from 70% to 85%, very advantageously at a concentration of 80% by weight relative to the total weight of the aqueous solution comprising the extract.

In one alternative embodiment of the invention, the extract will be solubilized and/or diluted in a solvent, in particular a polar solvent, such as water, an alcohol, a polyol, a glycol, such as pentylene glycol and/or butylene glycol and/or hexylene glycol and/or caprylyl glycol, or a mixture thereof, preferentially an aqueous-glycolic mixture, more preferentially containing a glycol chosen from hexylene glycol, caprylyl glycol and mixtures thereof. Advantageously, the extract obtained is diluted and/or soluble in an aqueous solution containing hexylene glycol, in particular containing between 0.1% and 10% by weight of hexylene glycol, preferentially between 0.5% and 5% by weight of hexylene glycol, relative to the total weight of the cosmetic ingredient. Advantageously, the extract obtained is diluted and/or soluble in an aqueous solution containing caprylyl glycol, in particular containing between 0.01% and 5% by weight of caprylyl glycol, preferentially between 0.1% and 1% by weight of caprylyl glycol, relative to the total weight of the aqueous solution comprising the extract. In particular, the aqueous solution in which the *N. lappaceum* extract is solubilized according to the invention comprises xanthan gum, in particular between 0.01% and 5% by weight of xanthan gum, relative to the total weight of the aqueous solution, more particularly between 0.1% and 1% by weight of xanthan gum relative to the total weight of the aqueous solution comprising the extract. Advantageously, the solution in which the *N. lappaceum* extract is solubilized according to the invention comprises hexylene glycol, caprylyl glycol and xanthan gum.

The extract can also be present in a cosmetic composition further comprising at least one cosmetically acceptable excipient. The term "acceptable" is intended to mean a cosmetic excipient or excipient non-irritating to the skin, which does not induce an allergic response and is chemically stable.

A subject of the present invention thus relates to the use of the pericarp extract of *N. lappaceum* in a cosmetic composition, for maintaining and/or increasing the hydration and/or the barrier effect of skin and/or of mucous membranes, advantageously dry skin and/or dry mucous membranes. The cosmetic composition may be administered topically or orally, in particular in the form of gel capsules, capsules or gel.

Advantageously, it will be applied topically to all or part of the body and/or of the face and/or the mucous membranes, advantageously chosen from the legs, feet, underarms, hands, thighs, stomach, chest, neck, arms, torso, back, labial mucous membrane, face and/or scalp, more advantageously the chest and/or face, even more advantageously the face. Advantageously, the composition will be applied to healthy dry skin and/or healthy dry mucous membranes.

In one embodiment of the invention, the extract according to the invention is present in the cosmetic or dermatological composition at a concentration of $1\times10^{-4}$% to 10%, preferentially from $1\times10^{-4}$% to 5%, and more preferentially from $1\times10^{-3}$% to 3% by weight, relative to the total weight of the composition.

The excipient(s) may be chosen from surfactants and/or emulsifiers, preservatives, buffers, chelating agents, denaturing agents, opacifiers, pH adjusters, reducing agents, stabilizers, thickeners, gelling agents, film-forming polymers, fillers, mattifying agents, gloss agents, pigments, dyes, fragrances and mixtures thereof. The CTFA (Cosmetic Ingredient Handbook, Second Edition (1992)) describes various cosmetic excipients suitable for use in the present invention.

Advantageously, the excipient(s) are chosen from the group comprising polyglycerols, esters, cellulose polymers and derivatives, lanolin derivatives, phospholipids, lactoferrins, lactoperoxidases, saccharose-based stabilizers, vitamin E and its derivatives, xanthan gums, natural and synthetic waxes, vegetable oils, triglycerides, unsaponifiables, phytosterols, silicones, protein hydrolyzates, betaines, aminoxides, plant extracts, saccharose esters, titanium dioxides, glycines, and parabens, and more preferably from the group consisting of steareth-2, steareth-21, glycol-15 stearyl ether, cetearyl alcohol, phenoxyethanol, methylparaben, ethylparaben, propylparaben, butylparaben, butylene glycol, caprylyl glycol, natural tocopherols, glycerin, dihydroxycetyl sodium phosphate, isopropyl hydroxyketyl ether, glycol stearate, triisononanoine, octyl cocoate, polyacrylamide, isoparaffin, laureth-7, a carbomer, propylene glycol, hexylene glycol, glycerol, bisabolol, dimethicone, sodium hydroxide, PEG 30-dipolyhydroxysterate, capric/caprylic triglycerides, cetearyl octanoate, dibutyl adipate, grape seed oil, jojoba oil, magnesium sulfate, EDTA, a cyclomethicone, xanthan gum, citric acid, sodium lauryl sulfate, waxes and mineral oils, isostearyl isostearate, propylene glycol dipelargonate, propylene glycol isostearate, PEG 8, beeswax, glycerides of hydrogenated palm heart oil, lanolin oil, sesame oil, cetyl lactate, lanolin alcohol, castor oil, titanium dioxide, lactose, saccharose, low density polyethylene, an isotonic saline solution, and mixtures thereof.

The cosmetic composition according to the invention may be chosen from an aqueous or oily solution, a cream or an aqueous gel or an oily gel, especially a shower gel, a milk, an emulsion, a microemulsion or a nanoemulsion, which is especially oil-in-water or water-in-oil or multiple or silicone-based, a mask, a serum, a lotion, a liquid soap, a dermatological bar, an ointment, a foam, a patch, an anhydrous product, which is preferably liquid, pasty or solid, for example in the form of makeup powders, a rod or a stick, in particular in the form of a lipstick. Advantageously, it is a cream or a serum.

The cosmetic composition may also comprise other ingredients which are active on hydration of the skin and/or of the mucous membranes, inducing a supplementary or synergistic effect with the extract according to the invention, chosen from those which reinforce the barrier function and decrease insensible water losses and/or those which increase the water content of the skin and/or of the mucous membranes and/or stimulate aquaporin synthesis in order to improve the circulation of water in the cells. Mention will thus be made of serine, urea and its derivatives, the products sold under the name Marine Filling Spheres™, Advanced moisturizing Complex™, Hyaluronic Filling Spheres™, vegetal filling Spheres™, Osmogelline™, Micropatch™, PatcH20™, alkylcelluloses, lecithins, sphingoid-based compounds, ceramides, phospholipids, cholesterol and its derivatives, glycosphingolipids, phytosterols (stigmasterol et beta-sitosterol, campesterol), essential fatty acids, 1-2 diacylglycerol, 4-chromanone, pentacyclic triterpenes, such as ursolic acid, petroleum jelly, lanolin, sugars, in particular trehalose and its derivatives, rhamnose, fructose, maltose, lactose, erythritol, le mannitol, le D-xylose and glucose, adenosine and its derivatives, sorbitol, polyhydric alcohols, which are advantageously $C_2$-$C_6$, and more advantageously $C_3$-$C_6$, such as glycerin, propylene glycol, 1,3-butylene glycol, dipropylene glycol, diglycerin, polyglycerin and their mixture, glycerol and its derivatives, glyceryl polyacrylate, sodium lactate, pentanediol, serine, lactic acids, AHAs, BHAs, sodium pidolate, xylitol, sodium lactate, ectoin and its derivatives, chitosan and its derivatives, collagen, plankton, steroid derivatives (including DHEA, its 7-oxidized and/or 17-alkylated derivatives and sapogenins), methyl dihydrojasmonate, vitamine D and its derivatives, an extract of *Malva sylvestres* or an extract of *Centella asiatica*, acrylic acid homopolymers, beta-glucan and in particular sodium carboxymethyl beta-glucan, a C-glycoside derivative such as those described in application WO 02/051828, a rose musk oil, an extract of the microalga *Prophyridium cruentum* enriched with zinc, sold by Vincience under the name Algualane Zinc™, arginine, acetyl hexapeptide sold by Lipotech under the name Diffuporine™, the hydrolysate of *Viola tricolor* sold by Silab under the name Aquaphyline™, or a polysaccharide extracted from *Cassia angustifolia* seeds, sold under the name Hyalurosmooth™ by the applicant, a fermented hydrolysate of *Saccharomryces cerevisiae* sold under the name Relipidium™, or else one or more of the compounds of Natural Moisturizing Factor or a natural extract of honey sold by the applicant under the name Melhydran™. Other types of active agents may be present in the composition, such as anti-aging ingredients and/or bleaching active agents, antipollution ingredients and/or ingredients which promote the radiance of the complexion.

These may for example be a leaf extract of *Cassia alata* sold under the name DN-Age™ and/or an extract of lychees sold under the name Litchiderm™ as antioxidant active agents, a combination of an extract of *Salvia miltiorhizza* and of niacinamide, sold under the name CollRepair™ as a deglycating agent, an antiwrinkle extract of chicory, sold under the name Lox-Age™, an extract of *Achillea millefolium* sold under the name Neurobiox™, an extract of *Polygonum bistorta* sold under the name Perlaura™, an extract of galanga sold under the name Hyalufix™, an extract of corn sold under the name Deliner™ or an extract of *Voandzeia subterranea* sold under the name Epigenist™ by the applicant or else active agents which promote the firmness of the skin, such as a synthetic tetrapeptide sold under the name Dermican™, an extract of *Hibiscus abelmoschus* sold under the name Linefactor™, a purified extract of pea sold under the name Proteasyl™, an extract of *Manilkara multinervis* sold under the name Elestan™ a pulp extract of Argan sold under the name Argassential™ by the applicant. An extract of the *Origanum majorana* plant sold under the name Dermagenist™ and/or an extract of *Khaya senegalensis* sold under the name Collalift®18 may also be added to the cosmetic composition.

As antipollution agents and/or agents which promote the radiance of the skin, mention will be made an extract of argan oil sold under the name Arganyl™ and a seed extract of *Moringa oleifera* sold under the name Purisoft™ by the applicant.

Another subject of the invention relates to a cosmetic care process comprising the topical or oral, advantageously topical, administration of the extract according to the invention or of a cosmetic composition comprising it, for maintaining and/or increasing the hydration and/or the barrier effect of healthy skin and/or healthy mucous membranes, advantageously healthy dry skin and/or healthy dry mucous membranes. Thus, said process makes it possible to increase involucrin synthesis and/or hyaluronic acid content in the skin and/or the mucous membranes.

In one embodiment of the invention, the process consists of the topical application of the extract according to the invention or of the cosmetic composition comprising it, to all or part of the body and/or of the face and/or the mucous membranes, advantageously chosen from the legs, feet, underarms, hands, thighs, stomach, chest, neck, arms, torso, back, labial mucous membrane, face and/or scalp, more advantageously the chest and/or face, even more advantageously the face.

Advantageously, the process consists of the topical application of the extract according to the invention or the cosmetic composition comprising it, to dry skin and/or dry mucous membranes.

In an alternative embodiment of the invention, the cosmetic care process makes it possible to increase the radiance of the skin complexion, in particular by increasing the synthesis of ATP and/or of the taurine transporter TAUT in the skin.

A final subject of the invention relates to the pericarp extract *N. lappaceum* or a pharmaceutical, preferentially dermatological, composition, comprising it, for use, preferentially dermatological use, thereof in the prevention and/or treatment of pathological conditions caused by a state of abnormal dryness of the skin and/or of the mucous membranes, such as atopic dermatitis, cracking, eczema and/or ichthyosis.

Thus, a method is provided for the prevention and/or treatment of pathological conditions caused by a state of abnormal dryness of the skin and/or of the mucous membranes, such as atopic dermatitis, cracking, eczema and/or ichthyosis, comprising the administration of a pericarp extract of *N. lappaceum* or of a pharmaceutical, preferentially dermatological, composition comprising it.

Finally, also considered is the use of a pericarp extract of *N. lappaceum* or a pharmaceutical, preferentially dermatological, composition comprising it, for the production of a medicament, preferentially a dermatological medicament, intended for the prevention and/or treatment of pathological conditions caused by a state of abnormal dryness of the skin and/or of the mucous membranes, such as atopic dermatitis, cracking, eczema and/or ichthyosis.

The term "state of abnormal dryness" is intended to mean herein a state of pathological dryness requiring a therapeutic treatment.

In one embodiment of the invention, the extract is included in the pharmaceutical, preferentially dermatological, composition which also comprises at least one pharmaceutically or dermatologically acceptable excipient. Advantageously, the extract is present in the composition at a concentration by weight of from $1 \times 10^{-4}\%$ to 10% relative to the total weight of the composition, advantageously from $1 \times 10^{-3}\%$ to 3%, more advantageously from 0.01% to 3% by weight relative to the total weight of the composition.

Examples which refer to the description of the invention are presented below. These examples are given for illustrative purposes and could in no way limit the scope of the invention. Each of the examples has a general scope. The examples are an integral part of the present invention, and any feature appearing to be novel over any prior art whatsoever, from the description taken in its entirety, including the examples, is an integral part of the invention.

EXAMPLE 1: METHODS FOR PREPARING AN EXTRACT OF *N. LAPPACEUM* ACCORDING TO THE INVENTION

Example 1a) An amount of 10% by weight of dried pericarp of *N. lappaceum* relative to the total weight of pericarp and water as sole solvent was extracted by maceration for a period of 1 hour at a temperature of 20° C. The extract obtained was decanted and centrifuged, then the supernatant was filtered. The extract is in liquid form.

Example 1b) An amount of 10% by weight of dried pericarp of *N. lappaceum* relative to the total weight of solvent and pericarp was extracted by maceration in a water/ethanol mixture (30, 70; v/v) for a period of 1 hour at a temperature 80° C. The crude extract was decanted and centrifuged, then the supernatant was filtered. The extract is in liquid form.

Example 1c) An amount of 5% by weight of dried pericarp of *N. lappaceum* relative to the total weight of pericarp and water as sole solvent was extracted by maceration for a period of 1 hour at a temperature of 20° C. The extract obtained was decanted and centrifuged, then the supernatant was filtered. The extract is in liquid form.

Example 1d) An amount of 10% by weight of dried pericarp of *N. lappaceum* relative to the total weight of pericarp and water as sole solvent was extracted under subcritical conditions, at a temperature of 120° C., under a pressure of 250 bar. The crude extract is decanted, centrifuged and then filtered. The extract is in liquid form.

EXAMPLE 2: HYDRATING EFFECT OF THE EXTRACT OF *N. LAPPACEUM*

Example 2a) Increase in Involucrin Synthesis

Protocol:

Normal, that is to say non-pathological, human keratinocytes were cultured in an MCDB153 medium (Dutscher France) containing 2% of fetal calf serum. After culture for 3 days at 37° C., the growth medium was replaced with MCDB153 medium containing various final concentrations of extract of *N. lappaceum* (by weight relative to the total volume of the medium) or without extract (Control) (table 1). The culture medium was replaced then solubilized in an extraction buffer. The amount of involucrin was quantified by ELISA assay. The results obtained are expressed as % relative to the control (n=3) (MEAN: mean; SD: Standard deviation).

The various extracts were prepared as follows:

Leaf extract: An amount of 10% by weight of dried leaves of *N. lappaceum* relative to the total weight of leaves and of water extracted was extracted by maceration in water as sole solvent at ambient temperature, that is to say at 20° C., for a period of 1 hour. The extract is then decanted and centrifuged, then the supernatant is filtered. The extract is in liquid form.

Seed extract: An amount of 5% by weight of seeds of *N. lappaceum* relative to the total weight of seeds and of solvent was extracted by maceration in a water/ethanol mixture (70, 30; v/v) as sole solvent at a temperature of 80° C. for a period of 1 hour. The extract is then decanted and centrifuged, then the supernatant is filtered. The extract is in liquid form.

Branch extract: The extract was obtained by maceration using an amount of 10% by weight of dried branch of the *N. lappaceum* plant, relative to the total weight of branch and of water as sole solvent, at a temperature of 80° C., for a period of 1 hour. The crude extract was decanted, centrifuged and then filtered.

TABLE 1

|  | MEAN | SD |
|---|---|---|
| Control | 100 | 4 |
| Pericarp extract of *N. lappaceum* Example 1a) 0.01% (w/v medium) | 115 | 4 |
| Pericarp extract *N. lappaceum* Example 1a) 0.03% (w/v medium) | 145 | 8 |
| Seed extract of *N. lappaceum* 0.1% (w/v medium) | 86 | 2 |
| Leaf extract of *N. lappaceum* 0.001% (w/v medium) | 93 | 17 |
| Branch extract of *N. lappaceum* 0.001% (w/v medium) | 82 | 16 |

Conclusion:

The pericarp extract increased involucrin synthesis by at least 7% and up to 57% in comparison with the control, demonstrating its capacity to increase the hydration of the skin and/or of the mucous membranes. The pericarp extract showed a greater increase in involucrin synthesis than the other extracts of the *N. lappaceum* plant, that is say the other parts of the plant, in particular the seeds, demonstrating the advantage of the use of the pericarp for increasing the hydration of the skin.

Example 2b) Increase in Hyaluronic Acid Synthesis

Protocol:

Normal human keratinocytes were cultured in an MCDB153 medium (Dutscher France) containing 2% of fetal calf serum. After culture for 3 days at 37° C., the growth medium was replaced with MCDB153 medium containing a given concentration (final concentration by weight relative to the total volume of the medium) of extract of *N. lappaceum* (table 2) or without extract (Control).

The quantification of the hyaluronic acid was carried out on the filtered culture medium by the immunochemical technique (Echelon K-1200 Hyaluronic Acid ELISA Kit).

The various extracts of *N. lappaceum* were prepared as described in example 2a). The pericarp extract is the one described in example 1a). The pulp extract was obtained by maceration in water as sole solvent at ambient temperature, that is to say at 20° C., for a period of 1 hour, using an amount of 10% by weight of dried pulp of *N. lappaceum* relative to the total weight of pulp and of water. The crude extract was then decanted, then centrifuged and filtered.

TABLE 2

|  | MEAN | SD |
| --- | --- | --- |
| Control | 100 | 12 |
| Pericarp extract of *N. lappaceum* Ex 1a) 0.03% (w/v medium) | 149 | 18 |
| Pericarp extract of *N. lappaceum* Ex 1a) 0.2% (w/v medium) | 171 | 11 |
| Pulp extract of *N. lappaceum* 0.1% (w/v medium) | 125 | 18 |
| Seed extract of *N. lappaceum* 0.1% (w/v medium) | 124 | 15 |
| Leaf extract of *N. lappaceum* 0.001% (w/v medium) | 94 | 9 |
| Branch extract of *N. lappaceum* 0.001% (w/v medium) | 87 | 8 |

Conclusion:

the pericarp extract increased hyaluronic acid synthesis in the human keratinocytes by at least 19% and up to 94%, demonstrating its capacity to increase the hydration of the skin and the barrier effect of the skin and/or the mucous membranes. The pericarp extract showed a greater increase in hyaluronic acid synthesis than the extracts of other parts of the plant, in particular the pulp extract and the seed extract, demonstrating the advantage of using the pericarp for increasing the hydration and/or the barrier effect of the skin and/or of the mucous membranes.

Example 2c) Absence of Stimulation of Involucrin Synthesis by Ellagic Acid or Geranin Protocol:

Normal, that is to say non-pathological, human keratinocytes were cultured in an MCDB153 medium (Dutscher France) containing 2% of fetal calf serum. After culture for 3 days at 37° C., the growth medium was replaced with MCDB153 medium containing two final concentrations of ellagic acid or of geranin (w/v final medium) or without ellagic acid or without geranin (Control) (table 3). The culture medium was replaced. The amount of involucrin was quantified by ELISA assay. The results obtained are expressed as % relative to the control (n=3).

TABLE 3

|  | MEAN (% involucrin detected) | SD |
| --- | --- | --- |
| Control | 100 | 17 |
| Ellagic acid $1.1 \times 10^{-4}$% (w/v medium) | 68 | 14 |
| Ellagic acid $1.9 \times 10^{-4}$% (w/v medium) | 32 | 8 |
| Geranin $9 \times 10^{-4}$% (w/v medium) | 78 | 15 |
| Geranin $1.5 \times 10^{-3}$% (w/v medium) | 29 | 5 |

Conclusion:

Neither ellagic acid nor geranin stimulated involucrin synthesis at the concentrations tested, corresponding to the concentrations of geranin and ellagic acid present in the cosmetic ingredient of example 4. Neither ellagic acid nor geranin is thus responsible for the maintaining and/or the increasing of the hydration and/or the barrier effect of the skin and/or of the mucous membranes.

Example 2d) In Viva Measurement of the Increase in the Hydration of the Skin by the Extract According to the Invention Protocol:

The in vivo measurement of the hydration of the skin of a population of 27 women was carried out by measurement by capacitance using the MoistureMap MM100® instrument (Courage & Khazaka) at the times T14 (2 weeks) and T28 (4 weeks) after application to one cheek of a cosmetic formulation comprising 2% (w/v) of the active ingredient as described in example 4. The same measurement was carried out on the other cheek of the same population after application of a placebo cream not comprising the cosmetic ingredient of example 4.

TABLE 4

|  | % hydration T14 | % hydration T28 |
| --- | --- | --- |
| Control | 0 | 4.0 |
| Active ingredient Ex 4 | 3.0 | 7.0 |

Conclusion:

The cream comprising the active ingredient made it possible to increase the hydration of the skin of the population analyzed by at least 3% relative to the percentage hydration measured in the presence of the placebo cream.

EXAMPLE 3: INCREASE IN THE RADIANCE OF THE SKIN COMPLEXION BY THE EXTRACT ACCORDING TO THE INVENTION

Example 3a) ATP Synthesis

Protocol:

Normal, that is to say non-pathological, human fibroblasts were incubated for 3 days at 37° C. ($CO_2$=5%, 95% relative humidity) on a growth medium comprising DMEM (Dulbecco's Modified Eagle's Medium) and 10% of fetal calf serum. The medium was replaced with a Hanks saline solution (H8264, Sigma France) containing the pericarp extract prepared according to example 1c) at two final concentrations by volume relative to the total volume of the medium. After an incubation period of 24 hours, the cells were irradiated under UVA and then returned to culture for a period of 24 hours, at 37° C.

The cellular ATP was extracted with DMSO and assayed on an aliquot of the extract.

TABLE 5

|  | MEAN | SD |
|---|---|---|
| Control | 100 | 12 |
| Pericarp extract of *N. lappaceum* Example 1c) 0.25% (v/v medium) | 222 | 27 |
| Pericarp extract of *N. lappaceum* Example 1c) 0.5% (v/v medium) | 195 | 19 |

Conclusion:

The pericarp extract according to the invention increased ATP synthesis by at least 60% and up to 170% in the human fibroblasts.

Example 3b) Stimulation of the Synthesis of the Torino Transporter Taut

Protocol:

Normal human keratinocytes were cultured to confluence in an MCDB153 medium (Dutscher France) containing 2% of fetal calf serum. The cells were incubated for a period of 24 hours in the presence of the pericarp extract prepared according to example 1c) at a final concentration in the medium of 0.2% by volume relative to the total volume of the medium, or without extract (Control).

The cells were lyzed, then the TAUT protein content was quantified by ELISA assay. The total protein content was quantified by the Bradford method. The results are expressed in ng of TAUT per mg of protein (n=3).

TABLE 6

|  | MEAN |
|---|---|
| Control | 100 |
| Pericarp extract of *N. lappaceum* Example 1c) 0.2% (w/v medium) | 184.4* |

*mean significantly different than that of the control (p < 0.05)

Conclusion:

the pericarp extract increased the TAUT protein synthesis by at least 80% in the human keratinocytes, demonstrating its energizing active agent properties.

EXAMPLE 4: COSMETIC ACTIVE INGREDIENT

| Pericarp extract Example 1a) | 0.5% |
|---|---|
| Glycerin | 80% |
| Water | 19.5% |

EXAMPLE 5: FORMULATION EXAMPLES

Example 5a): Composition According to the Invention in the Form of a Body and Face Serum

| Phase | Name | Amount (% by total weight) |
|---|---|---|
| A | Water | 94.75 |
| A | Preservative | qs 100 |
| A | Glycerin | 1.00 |
| B | Xanthan gum | 0.2 |
| B | Sodium polyacrylate | 0.25 |
| C | Cosmetic ingredient according to example 4 | 2 |

Example 5b): Face Cream

The composition below is prepared according to methods known to those skilled in the art, in particular as regards the various phases to be mixed together. The amounts indicated are as percentage by weight relative to the total weight of the composition.

| Cosmetic ingredient according to example 4 | 3.00 |
|---|---|
| Xanthan gum | 0.50 |
| EDTA | 0.05 |
| Steareth-2 | 2.00 |
| Steareth-21 | 2.50 |
| Cetearyl alcohol | 1.00 |
| Propylheptyl caprylate | 15.00 |
| Sodium hydroxide (30% in solution) | 0.10 |
| Mixture of phenoxyethanol, chlorphenesin, benzoic acid, butylene glycol, sorbic acid (Germazide ™ PBS) | 1.25 |
| Mixture of polyacrylate-X, isohexadecane and polysorbate 60 (Sepigel ™ SMS 60) | 4.00 |
| Water | qs 100 |

The invention claimed is:

1. A cosmetic use care method for maintaining and/or increasing the hydration and/or the barrier effect of healthy akin and/or of healthy mucous membranes in a human comprising topically or orally administering an effective amount of a composition comprising 0.001 to 0.015% by weight of a pericarp extract of *Nephelium lappaceum*, based on the composition, wherein the pericarp extract is obtained by the steps of:
   (a) extracting *Nephelium lappaceum* pericarp in an extraction solvent consisting of water in an amount of 1 to 10 wt % pericarp based on the total of water and pericarp at a temperature of 4 to 25° C. for 30 minutes to 12 hours, and
   (b) removing the water by drying, decanting, centrifuging, or filtering to produce said pericarp extract.

2. The cosmetic use care method as claimed in claim 1, wherein the pericarp extract increases involucrin synthesis and/or the hyaluronic acid content in the skin and/or the mucous membranes.

3. The method as claimed in claim 1, wherein the composition is applied to healthy dry skin and/or healthy dry mucous membranes.

4. The method as claimed in claim 1, wherein the extract increases the radiance of the skin complexion.

5. The method as claimed in claim 4, wherein the extract increases the synthesis of ATP and/or of the taurine transporter TAUT.

6. The method as claimed in claim 1, wherein the extract is solubilized in an aqueous solution containing glycerin.

7. The method as claimed in claim 1, such that it consists in the topical application of the extract or of the cosmetic composition, to all or part of the body and/or of the face and/or the mucous membranes.

8. The method as claimed in claim 1, wherein the extract is solubilized in an aqueous solution containing glycerin at a concentration of from 60% to 90% by weight relative to the total weight of the aqueous solution comprising the extract.

* * * * *